United States Patent
Weinfield et al.

(10) Patent No.: US 7,019,267 B2
(45) Date of Patent: *Mar. 28, 2006

(54) SAMPLE TRAY HEATER MODULE (75) Inventors: Todd A. Weinfield, Redwood City, CA (US); Gary Lim, San Francisco, CA (US); Donald R. Sandell, San Jose, CA (US); Kevin S. Bodner, Belmont, CA (US); Mark Borodkin, San Mateo, CA (US); Mark Oldham, Los Gatos, CA (US); Jon Hoshizaki, Cupertino, CA (US)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/120,797

(22) Filed: May 3, 2005

(65) Prior Publication Data
US 2005/0194371 A1    Sep. 8, 2005

Related U.S. Application Data (63) Continuation of application No. 10/359,665, filed on Feb. 6, 2003, now Pat. No. 6,906,292, which is a continuation-in-part of application No. 10/104,335, filed on Mar. 22, 2002, now Pat. No. 6,896,849, which is a continuation-in-part of application No. 09/552,301, filed on Apr. 18, 2000, now Pat. No. 6,419,827, which is a continuation-in-part of application No. 09/182,946, filed on Oct. 29, 1998, now Pat. No. 6,159,368.

(51) Int. Cl.
*H05B 3/22* (2006.01)
*C12M 1/38* (2006.01)
*B01L 7/00* (2006.01)

(52) U.S. Cl. .............. 219/428; 219/385; 219/540; 219/521; 435/288.4; 435/305.2

(58) Field of Classification Search ............. None
See application file for complete search history.

(56) References Cited

U.S. PATENT DOCUMENTS

| | | | |
|---|---|---|---|
| 3,463,322 | A | 8/1969 | Gerarde |
| 3,721,364 | A | 3/1973 | Lukaschewitz et al. |
| 4,167,875 | A | 9/1979 | Meakin |

(Continued)

FOREIGN PATENT DOCUMENTS

DE    40 22 792 A1    12/1986

(Continued)

OTHER PUBLICATIONS

"Genesis Robotic Microplate Processor," *TECAN*, Document No. 390981, pp. 1-8, (1997).

(Continued)

*Primary Examiner*—Joseph M. Pelham
(74) *Attorney, Agent, or Firm*—Kilyk & Bowersox, P.L.L.C.

(57) ABSTRACT

A heater module is described that includes a heat distribution plate including a bottom portion having first and second sides and a plurality of projections extending away from one of the sides. A heat source is provided for heating the heat distribution plate, and, optionally, a heating tray can be used to receive the heat source and heat distribution plate. The heater module is adapted to engage a sample purification tray having a plurality of purification and/or discharge columns which can extend through openings in the heater module and direct a sample into a sample receiving tray. Methods of heating samples using the heater module are also described.

15 Claims, 7 Drawing Sheets

U.S. PATENT DOCUMENTS

| | | | |
|---|---|---|---|
| 4,246,339 A | 1/1981 | Cole et al. | |
| 4,279,342 A | 7/1981 | Van Pelt | |
| 4,304,865 A | 12/1981 | O'Brien et al. | |
| 4,422,151 A | 12/1983 | Gibson | |
| 4,595,635 A | 6/1986 | Dubrow et al. | |
| 4,680,233 A | 7/1987 | Camin et al. | |
| 4,734,192 A | 3/1988 | Champion et al. | |
| D297,602 S | 9/1988 | Schnur | |
| 4,777,063 A | 10/1988 | Dubrow et al. | |
| 4,902,481 A | 2/1990 | Clark et al. | |
| 4,927,604 A | 5/1990 | Mathus et al. | |
| 4,948,442 A | 8/1990 | Manns | |
| 4,948,564 A | 8/1990 | Root et al. | |
| 4,950,546 A | 8/1990 | Dubrow et al. | |
| 4,969,306 A | 11/1990 | Wallin | |
| 5,002,889 A | 3/1991 | Klein | |
| 5,037,667 A | 8/1991 | Dubrow et al. | |
| 5,047,215 A | 9/1991 | Manns | |
| 5,079,300 A | 1/1992 | Dubrow et al. | |
| 5,108,703 A | 4/1992 | Pfost et al. | |
| 5,108,704 A | 4/1992 | Bowers et al. | |
| 5,110,556 A | 5/1992 | Lyman et al. | |
| 5,114,681 A | 5/1992 | Bertoncini et al. | |
| 5,116,496 A | 5/1992 | Scott | |
| 5,141,719 A | 8/1992 | Fernwood et al. | |
| 5,201,348 A | 4/1993 | Lurz | |
| 5,208,161 A | 5/1993 | Saunders et al. | |
| 5,227,137 A | 7/1993 | Monti et al. | |
| 5,264,184 A | 11/1993 | Aysta et al. | |
| 5,282,543 A | 2/1994 | Picozza et al. | |
| 5,283,039 A | 2/1994 | Aysta | |
| 5,326,533 A | 7/1994 | Lee et al. | |
| 5,342,581 A | 8/1994 | Sanadi | |
| 5,352,086 A | 10/1994 | Mank | |
| 5,368,729 A | 11/1994 | Stefkovich et al. | |
| 5,380,437 A | 1/1995 | Bertoncini | |
| 5,384,024 A | 1/1995 | Moring et al. | |
| 5,401,637 A | 3/1995 | Pocock | |
| 5,409,832 A | 4/1995 | Pocock | |
| 5,427,265 A | 6/1995 | Cautereels et al. | |
| 5,459,300 A | 10/1995 | Kasman | |
| 5,464,541 A | 11/1995 | Aysta et al. | |
| 5,475,610 A | 12/1995 | Atwood et al. | |
| 5,506,343 A | 4/1996 | Kufe | |
| 5,516,490 A | 5/1996 | Sanadi | |
| 5,582,665 A | 12/1996 | Eigen et al. | |
| 5,602,756 A | 2/1997 | Atwood et al. | |
| 5,604,130 A | 2/1997 | Warner et al. | |
| 5,620,663 A | 4/1997 | Aysta et al. | |
| 5,650,323 A | 7/1997 | Root | |
| 5,665,247 A | 9/1997 | Valus et al. | |
| 5,679,310 A | 10/1997 | Manns | |
| 5,681,492 A | 10/1997 | Van Praet | |
| 5,710,381 A | 1/1998 | Atwood et al. | |
| 5,721,136 A | 2/1998 | Finney et al. | |
| 5,736,105 A | 4/1998 | Astle | |
| 5,736,106 A | 4/1998 | Ishiguro et al. | |
| 5,741,463 A | 4/1998 | Sanadi | |
| 5,792,425 A | 8/1998 | Clark et al. | |
| 5,792,430 A * | 8/1998 | Hamper | 422/102 |
| 5,846,493 A | 12/1998 | Bankier et al. | |
| 5,929,138 A | 7/1999 | Mercer et al. | |
| 6,048,919 A | 4/2000 | McCullough | |
| 6,159,368 A | 12/2000 | Moring et al. | |
| 6,251,343 B1 | 6/2001 | Dubrow et al. | |
| 6,338,802 B1 | 1/2002 | Bodner et al. | |
| 6,419,827 B1 | 7/2002 | Sandell et al. | |
| 6,451,261 B1 | 9/2002 | Bodner et al. | |
| 6,503,457 B1 | 1/2003 | Neeper et al. | |
| 6,638,761 B1 * | 10/2003 | Shin et al. | 435/288.4 |
| 6,730,883 B1 | 5/2004 | Brown et al. | |

FOREIGN PATENT DOCUMENTS

| | | |
|---|---|---|
| DE | 297 22 473 U1 | 4/1998 |
| DE | 196 52 327 A1 | 6/1998 |
| EP | 0 359 249 A2 | 3/1990 |
| EP | 0 131 934 B1 | 12/1991 |
| EP | 0 645 187 A2 | 3/1995 |
| EP | 0 502 371 B1 | 8/1995 |
| EP | 0 676 643 A2 | 10/1995 |
| EP | 0 903 176 A2 | 3/1999 |
| EP | 0 925 828 A1 | 6/1999 |
| GB | 2 246 081 A | 1/1992 |
| JP | 06210189 | 2/1994 |
| WO | WO 86/07606 | 12/1986 |
| WO | WO 94/28111 | 12/1994 |
| WO | WO 95/30139 | 11/1995 |
| WO | WO 98/10853 | 3/1998 |
| WO | WO 00/25922 | 5/2000 |

OTHER PUBLICATIONS

"mRNA Isolation Using Event," *BIONEWS*, 01:3 (1996).

"Multiscreen[SM] Assay System," *Multiscreen[SM] Assay Systems, Rev. C. Updated*:Apr. 13, 1998, Publication P17479 Revision C. Internet Address: http//millispider.millipore.com/analytical/manuals/p17479a.htm, pp. 1-4.

International Search Report, mailed Jun. 25, 2004, for International Application No. PCT/US2004/002811 (3 pages).

Newell et al., "Overload, Tripping, and Stop Mechanisms," *Ingenious Mechanisms*, Industrial Press Inc., New York, pp. 109-111 (1967).

Product Information Sheet, Proportion-Air, Inc., Document No. SVQ100-A (1997).

Qiagen Product Guide, pp. 16, 37-38 (1997).

Ruppert, A. et al., *A Filtration Method for Plasmid Isolation Using Microtiter Filter Plates, Analytical Biochemistry*, pp. 230:130-134 (1995).

*Technical Data on Ultra-Pure QM-A Quartz Filters*, Whatman, Data Sheet No. 860 QM-AA (1992).

The Genesis Series of RSPs, *TECAN*, Document No. 390696, pp. 1-8 (1997).

*Whatman Ultra-Pure QM-A Filters*, Whatman, Data Sheet No. 860 QM-AA (1992).

\* cited by examiner

SAMPLE TRAY HEATER MODULE

CROSS REFERENCE TO RELATED APPLICATIONS

This application is a continuation application of U.S. patent application Ser. No. 10/359,665, filed Feb. 6, 2003 now U.S. Pat. No. 6,906,292, which is a continuation-in-part application of U.S. patent application Ser. No. 10/104,335, filed Mar. 22, 2002 now U.S. Pat. No. 6,896,849, which is a continuation-in-part of U.S. patent application Ser. No. 09/552,301, filed Apr. 18, 2000, now U.S. Pat. No. 6,419,827 B1, issued Jul. 16, 2002, which is a continuation-in-part of U.S. patent application Ser. No. 09/182,946, filed Oct. 29, 1998, now U.S. Pat. No. 6,159,368, issued Dec. 12, 2000. Cross reference is made to the following related applications which are divisional applications of U.S. patent application Ser. No. 09/182,946 filed Oct. 29, 1998, now U.S. Pat. No. 6,159,368, issued Dec. 12, 2000: U.S. patent application Ser. No. 09/565,673, filed May 4, 2000, now U.S. Pat. No. 6,451,261 B1, issued Sep. 17, 2002; Ser. No. 09/565,202, filed May 4, 2000, now U.S. Pat. No. 6,506,343 B1, issued Jan. 14, 2003; and Ser. No. 09/565,566 filed May 4, 2000, now U.S. Pat. No. 6,338,802 B1, issued Jan. 15, 2002. All references cited herein are incorporated in their entireties by reference.

FIELD

The present invention relates to a multi-well microfiltration apparatus and methods for processing a plurality of fluid samples simultaneously at a desired temperature.

BACKGROUND

In recent years, microtitration wells have assumed an important role in many biological and biochemical applications, such as sample preparation, genome sequencing, and drug discovery programs. A variety of multi-well arrangements, constructed according to standardized formats, are now popular. Methods of heating samples in such multi-well arrangements, such as those described in U.S. Pat. No. 5,459,300 and U.S. Pat. No. 5,681,492, are known in the art, but do not perform consistent, uniform heating of all samples in a multi-sample array.

It is desirable to provide an apparatus for consistently and uniformly maintaining, raising, or lowering the temperature of a plurality of samples, to facilitate processing such as purification.

SUMMARY

According to various embodiments, a sample tray heater module that can be used on an automated or manual sample preparation station is described. According to various embodiments, the sample tray heater module can include a heat distribution plate and a heat source. According to various other embodiments, the sample tray heater module can further include a heating tray.

According to various embodiments, a system including a sample tray heater module is provided wherein the temperature of the sample tray heater module can be monitored and controlled during heating. According to various embodiments, the heater module is capable of heating a sample to a temperature in a range of from about 5° C. to about 100° C. In other embodiments, the heater module is capable of heating a sample to a temperature in a range of from about 20° C. to about 70° C. According to various embodiments, the heater module is capable of heating a sample at a rate of greater than or equal to about 1° C. per minute.

According to various embodiments, a system is provided wherein a sample tray heater module can be fitted with a sample purification tray, and/or a receiving well array, prior to processing samples.

According to various embodiments, a sample tray heater module is provided that includes a plurality of protrusions capable of interacting with a sample purification tray for proper positioning thereof relative to the heater module. The plurality of protrusions can provide uniform heating to a plurality of discharge columns of a sample purification tray according to various embodiments.

According to various embodiments, a sample tray heater module is provided that is inexpensive and reliable. According to various embodiments, the sample tray heater module can be disposable. According to various embodiments, the heat distribution plate, heat source, and optional heating tray of the heater module can each be made from a thermally conductive material such as a metal, metal alloy, or polymeric material, such as a thermoplastic, or a combination thereof.

A purification apparatus including a heater module for heating of a sample passing therethrough is described according to various embodiments.

According to various embodiments, a method is provided for purifying a sample wherein the sample is heated during purification.

Additional features and advantages of the heater module and its use will be set forth in part in the description that follows, and in part will be apparent from the description and drawings, or may be learned by practice. Objectives and other advantages of the heater module and methods of making and using the heater module will be realized and obtained by means of the elements and combinations described in the written description herein and the appended claims.

To achieve these and other advantages, a sample tray heater module is provided that includes a heat distribution plate and a heat source. The heat distribution plate can include a bottom portion and one or more protrusions extending away from the bottom portion. The heat source can be in contact with an underside of the bottom portion of the heat distribution plate. One or more electrical contacts can be in electrical communication with the heat source. Optionally, the heater module can include a heating tray adapted to receive the heat source and the heat distribution plate.

Other various embodiments of the present invention will be apparent to those skilled in the art from consideration of the specification and practice of the invention described herein. It is intended that the specification and examples be considered as exemplary only, and that the true scope and spirit of the invention include those other various embodiments.

DESCRIPTION OF CERTAIN EMBODIMENTS

According to various embodiments, a sample tray heater module is provided, for example, for a purification apparatus. The heater module can be used in or with an apparatus useful for purification, filtration, and/or separation of biological and/or chemical samples, such as DNA. The purification apparatus can include a sample purification tray having a plurality of discharge columns, each with a distal end, wherein each discharge column is adapted to receive or includes a filter medium. The sample purification tray can be, for example, a discharge conduit array, a sample purification array, or other device capable of receiving and allowing passage therethrough of a sample.

The sample purification tray can be disposed in a purification apparatus and held aligned with and in fluid communication with a receiving well array, for example, a sample well array, sample well tray, sample tray, array of receiving wells, or other device capable of receiving and containing, restraining, or holding a sample therein. The distal end of each discharge column of the sample purification tray can be in fluid communication with a respective receiving well of the receiving well array. The sample tray heater module, according to various embodiments, can be disposed between the sample purification tray and the receiving well array. The purification apparatus can be located in a carriage such that the sample purification tray is capable of horizontal and/or vertical movement with respect to the heating device and/or the receiving well array. Further details regarding exemplary sample purification trays, receiving well arrays, and purification apparatuses, and methods for the use thereof, are described in co-pending U.S. patent application Ser. No. 10/104,335, filed Mar. 22, 2002.

According to various embodiments, a sample tray heater module is provided that can include a heat distribution plate having a plurality of protrusions, and a heat source. The heat source can be in contact with a side of a bottom portion of the heat distribution plate. The sample tray heater module can include a plurality of through holes for nozzle tips passing through the heat distribution plate and the heat source.

The sample tray heater module can include a heating tray for holding the heat source and the heat distribution plate. The heating tray can be capable of receiving and aligning the heat source and heat distribution plate, and can include a plurality of through holes for nozzle tips corresponding to the through holes for nozzle tips in the heat distribution plate and the heat source. The heater module can be constructed from a thermally conductive material, for example, a metal such as aluminum or stainless steel, a thermally conductive polymer, or a combination thereof.

Figure 1:
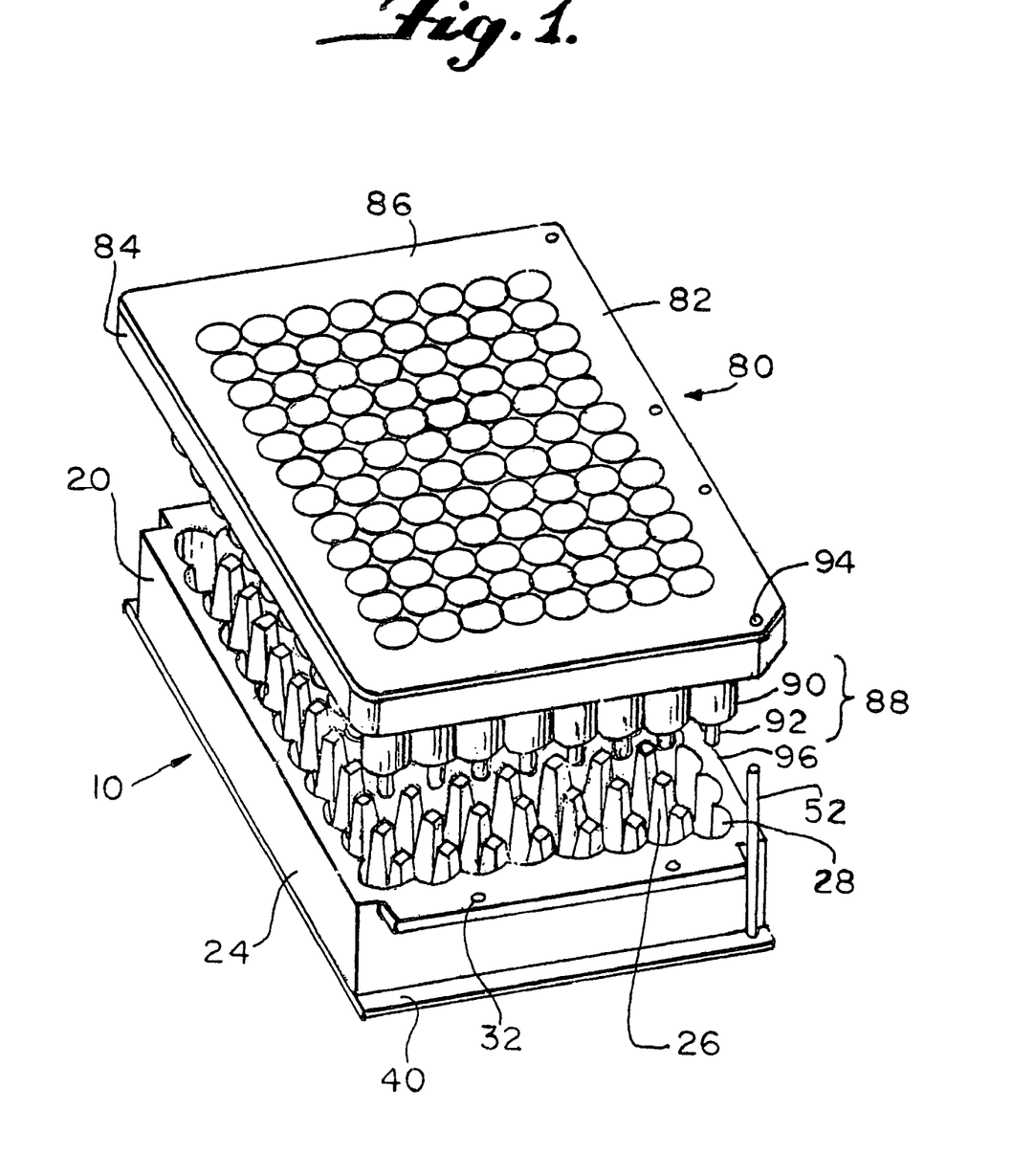
FIG. 1 is a perspective view of a sample purification tray and a heater module.
Figure 2:
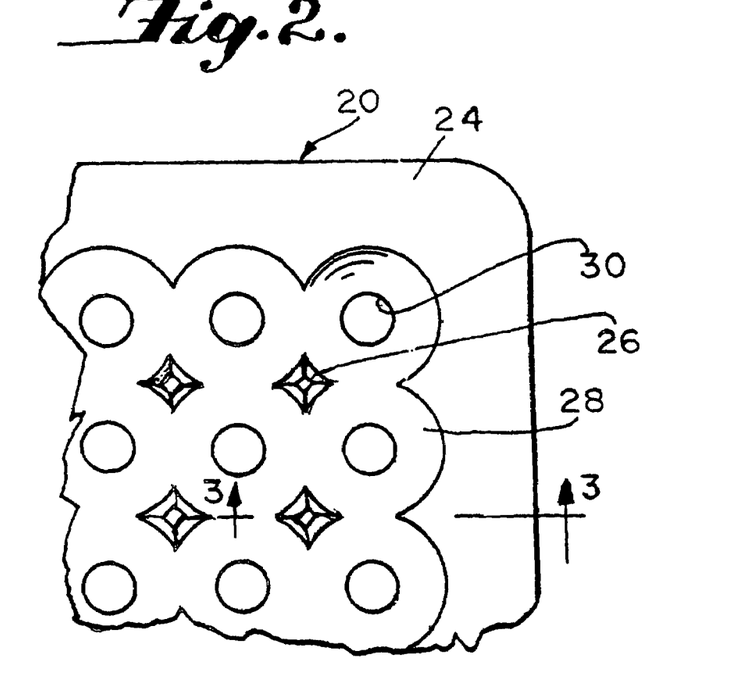
FIG. 2 is a top view of a heat distribution plate according to various embodiments.
Figure 3:
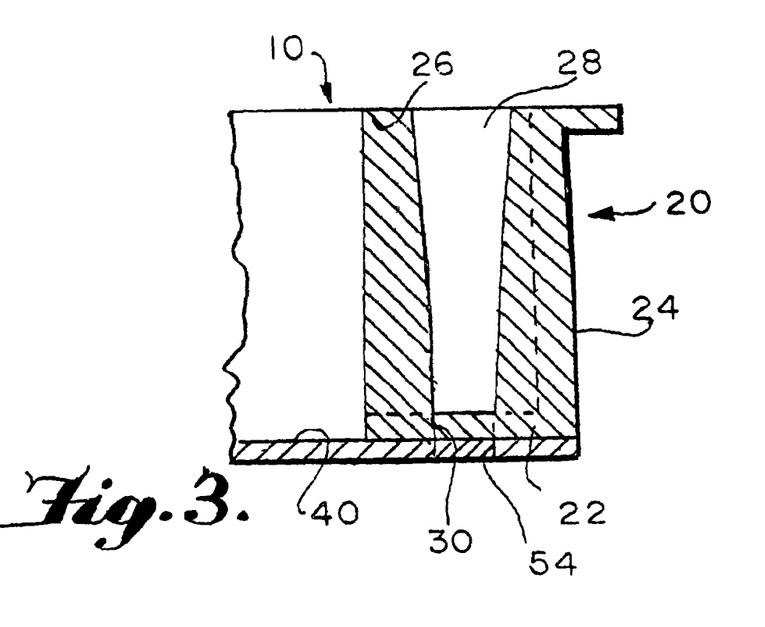
FIG. 3 is a sectional side view taken along line 3—3 in FIG. 2.
Figures 4, 5:
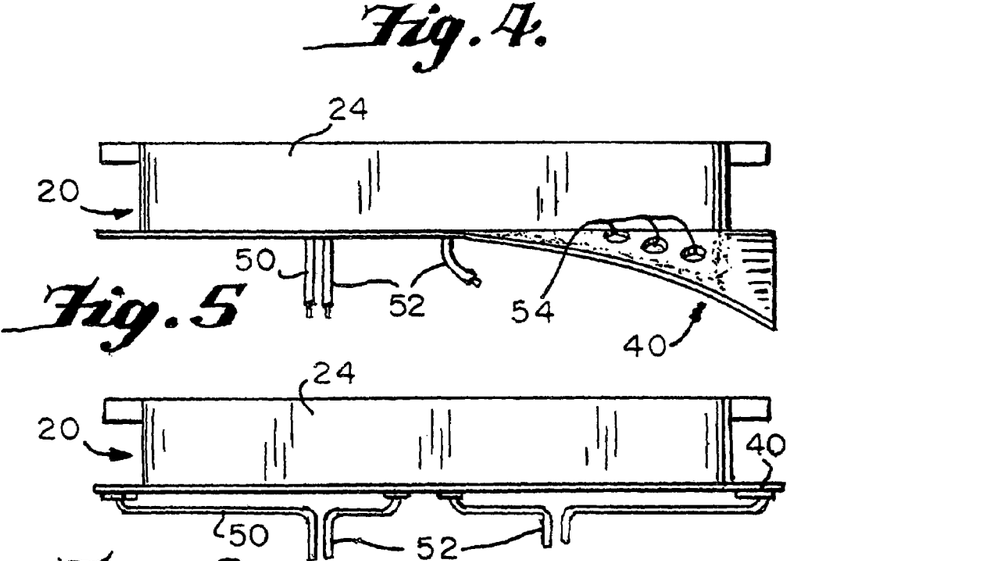
FIG. 4 is a front view of a heater module according to various embodiments.
FIG. 5 is a back view of the heater module shown in FIG. 4.

According to various embodiments, and as shown in FIGS. 1–3, the heater module 10 can comprise a heat distribution plate 20 having a bottom portion 22 having a first side and a second opposing side, and from which sidewalls 24 extend substantially perpendicularly or perpendicularly from the first side of bottom portion 22. Also extending from the first side of bottom portion 22 can be a plurality of protrusions 26. As used herein, "protrusion" refers to a projection, extension, elongation, or other raised feature extending out of a plane of bottom portion 22. The sidewalls 24 and each of the plurality of protrusions 26 can be the same height. The plurality of protrusions 26 and sidewalls 24 define a plurality of discharge column receptacles 28, for example, to accommodate a plurality of discharge conduits or columns from a discharge conduit array, for example, a sample purification tray 80. Each discharge column receptacle 28 can have a respective through hole 30 for a nozzle tip through which a discharge column nozzle tip can extend. The heat distribution plate 20 can include screw-through holes 32 as shown, tap holes, clips, or other devices useful for fastening the heater module together.

Figures 6, 9:
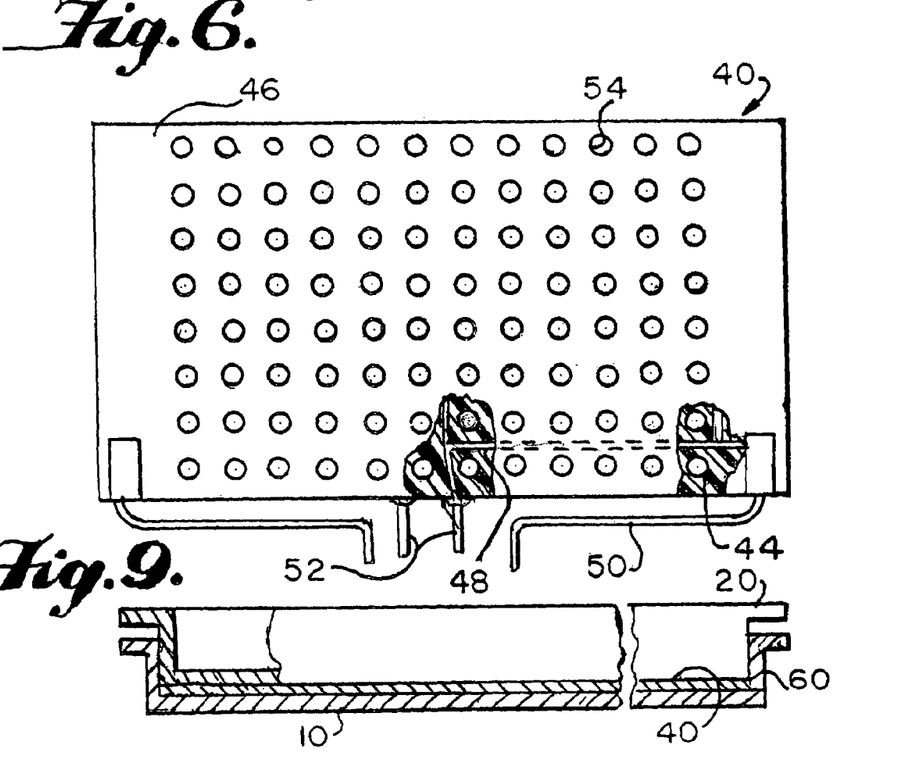
FIG. 6 is a bottom view of the heater module shown in FIGS. 4 and 5.
FIG. 9 is a side-sectional view of a heater module having a heating tray, a heat source, and a heat distribution plate.
Figure 7:
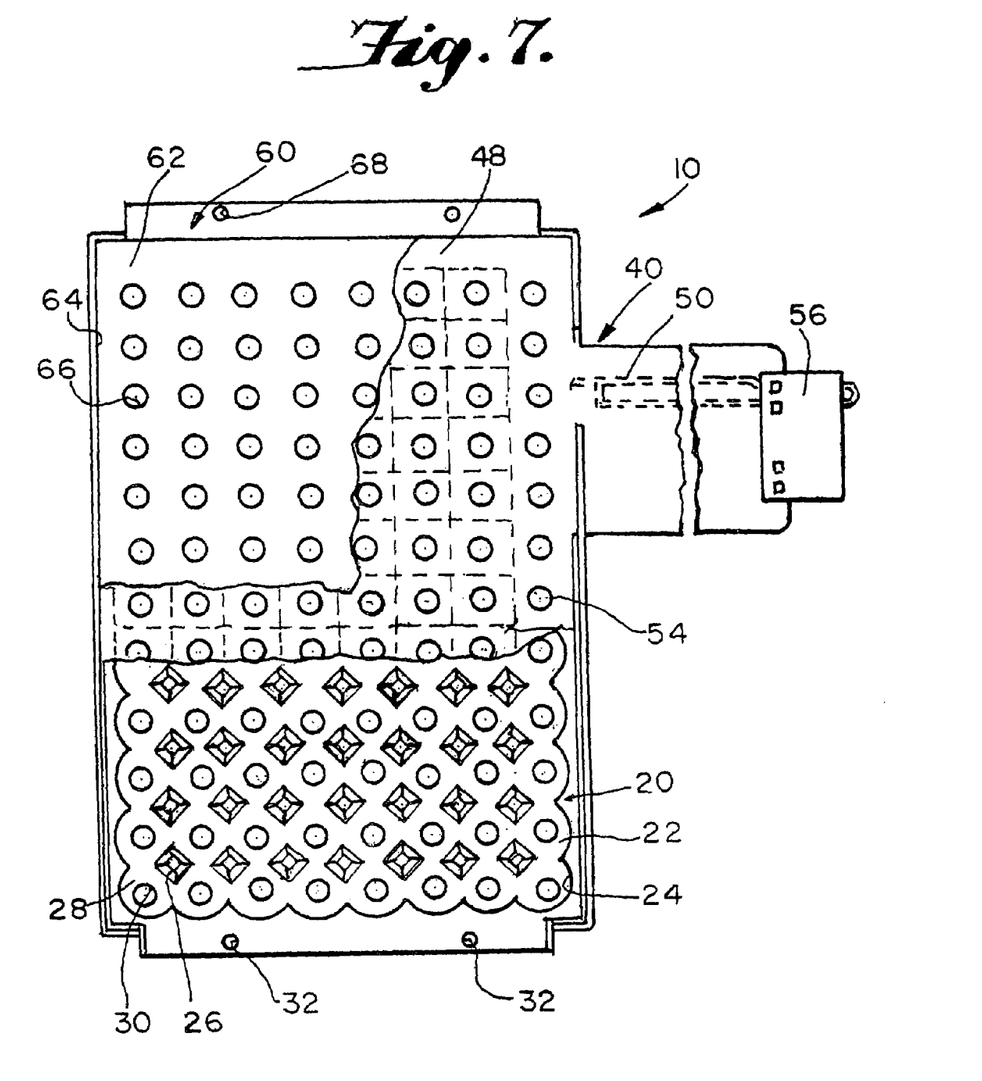
FIG. 7 is a cut-away top view of a heater module according to various embodiments taken along various cut-aways.
Figure 8:
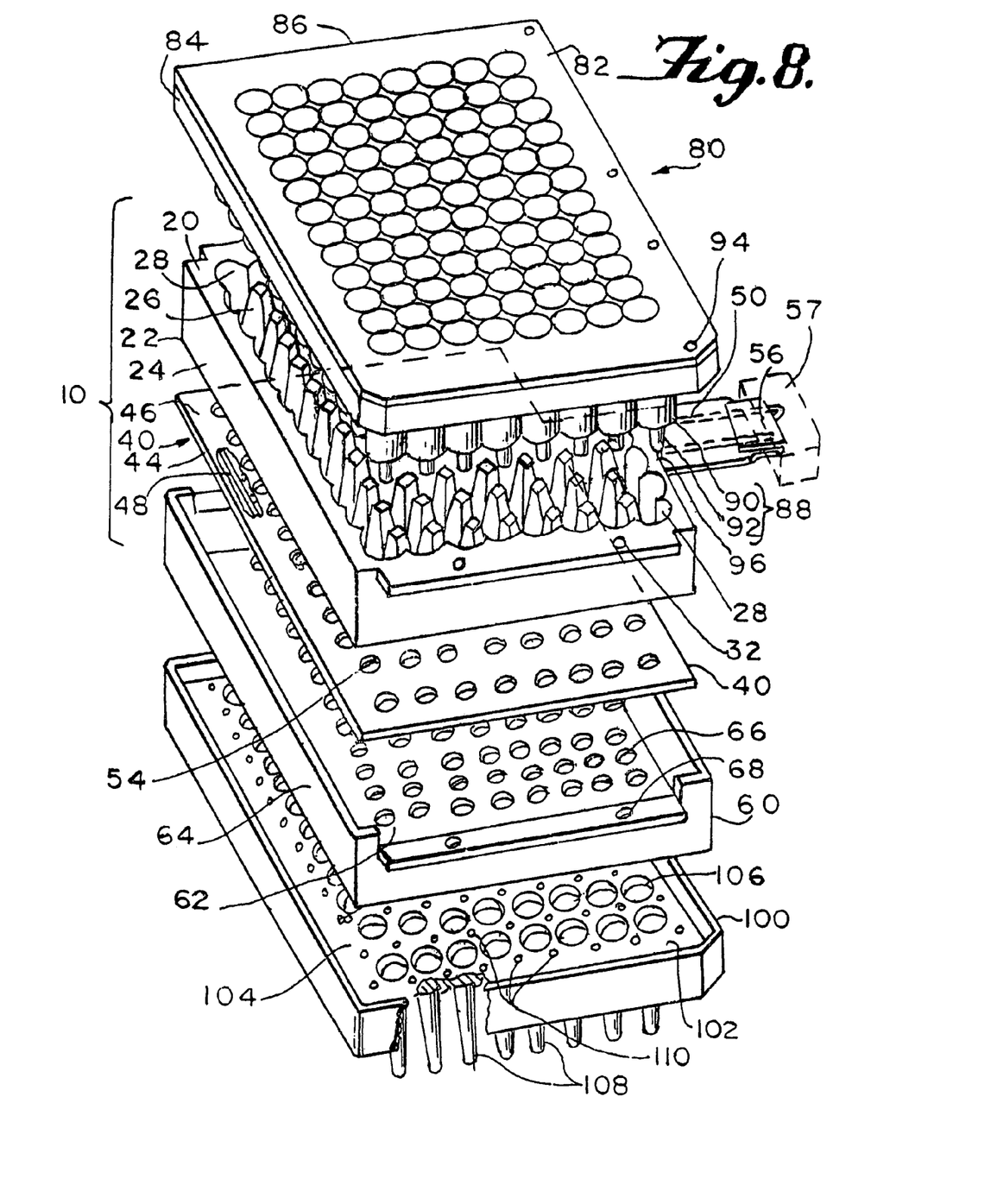
FIG. 8 is a perspective view of a purification apparatus having a sample purification tray, a heater module, and a sample well tray, wherein the heater module comprises a heat distribution plate, a heat source, and a heating tray.

As shown in FIGS. 1 and 4–7, a heat source 40 can be in contact with the second side of the bottom portion of the heat distribution plate 20. According to various embodiments, the heat source 40 can be a substantially flat material. The heat source 40 can include a bottom layer 44 in which can be disposed heating wires 50 for carrying power to a wire layout 48. The wire layout 48 can be attached to temperature sensor wires or contact wires 52. According to various embodiments, and as shown in FIG. 1, the temperature probes 52 and/or the wires 50 can extend through through holes 94 of sample purification tray 80 to secure the sample purification tray 80 to the heater module 10. For example, the temperature sensor can be a thermistor or a thermocouple, or the heating wires themselves can act as temperature sensors as, for example, measured based on resistivity through the wires. The bottom layer 44 of heat source 40 having the wire layout 48 disposed therein can be covered by cover layer 46 to protect the wires. The heat source 40 can have through holes 54 for nozzle tips to extend therethrough. The through holes 54 for nozzle tips can correspond to through holes 30 for nozzle tips of a heat distribution plate 10 and, optionally, can correspond to through holes 66 for nozzle tips of a tray 60. The power wires 50 can be connected to a controller 57 or connection module 56 as shown in FIGS. 7 and 8. The controller 57 can be connected to a power source to provide energy for heating the wires. The controller can include computer controls, thermal cut-offs, and/or PID controllers, or other controllers that can modify the current flowing through the heating elements and/or heating wires. The heat source 40 can be attached to or separate from the heat distribution plate 20. According to various embodiments, the heat source 40 can be incorporated in the heat distribution plate, for example, by integral molding therewith. The heat source 40 can be in contact with the first side of the bottom portion 22 of the heat distribution plate 20, wherein the first side of the bottom portion 22 includes the surfaces of the plurality of protrusions 26.

As shown in FIGS. 7, 8, and 9, the heater module 10 can further comprise a tray 60 having an inwardly facing bottom portion 62 from a first side of which sidewalls 64 extend substantially perpendicularly or perpendicularly. The tray 60 can be adapted to receive the heat source 40 and the heat distribution plate 20 within the area defined by sidewalls 64 and bottom portion 62. The tray 60 can have through holes 66 for nozzle tips corresponding to through holes 54 for nozzle tips of the heat source 40 and through holes 30 for nozzle tips of the heat distribution plate 20. Tray 60 can also comprise screw holes 68 for fastening together the heater module by screws, bolts, or other attachment devices passing through at least one screw-through hole 32 and at least one screw hole 68.

The heat distribution plate 20 can be capable of receiving a discharge conduit array, for example, a sample purification tray 80, as shown in FIGS. 1 and 8. Sample purification tray 80 can include a top plate 82 from a side of which sidewalls 84 extend substantially perpendicularly or perpendicularly. Sample purification tray 80 can have openings 86 in top plate 82, which openings lead into discharge columns 88. The discharge columns 88 can include more than one section, for example, a first portion 90 and a second portion 92, as shown in FIGS. 1 and 8. The discharge column 88 can terminate in a nozzle tip having a discharge opening 96 which is capable of fluid communication with a respective opening 106 in corresponding sample well tray or receiving well array 100, as shown in FIG. 8. At least the nozzle tips of discharge columns 88 can pass through respective through holes 30 for nozzle tips of the heat distribution plate, respective through holes 54 for nozzle tips of the heat source, and, optionally, respective through holes 66 for nozzle tips of the tray 60, to extend below heater module 10. The sample purification tray 80 can also have openings 94 to receive temperature probe 52 and/or power wires 50 from heat source 40.

The portions 90, 92 of the discharge columns 88 of the sample purification tray 80 can be formed separately and joined together by any suitable method, such as heat welding or adhesive bond, or they can be integrally formed such as by molding. Various methods of forming the sample purification tray will be apparent to those skilled in the art. The sample purification tray can be formed from a plastic material, a metal, or any other suitable material or combination of materials as known to those skilled in the art. The sample purification tray can be formed of a material which does not interact or react with the sample to be purified. Examples of suitable materials include polypropylene, polyethylene, polycarbonate, and mixtures thereof.

The sample purification tray 80 can be adapted to receive one or more filters in one or more of the discharge columns 88. Various sample purification trays and details regarding the size, shape, material, and manufacture of sample purification trays, discharge conduit arrays, and filters for use therein, can be found in co-pending U.S. patent application Ser. No. 10/104,335, U.S. Pat. No. 6,419,827 B1, and U.S. Pat. No. 6,159,368, all of which are herein incorporated in their entireties by reference.

The sample purification tray can fit snuggly into heat distribution plate 20 such that discharge columns 88 are in good, snug, thermal contact with the protrusions of heat distribution plate 20. The regions between adjacent projections are referred to herein as discharge column receptacles 28. According to various embodiments, a portion of at least one of the plurality of protrusions 26 separates each discharge column 88 from the next discharge column 88. According to various embodiments, at least a portion of a discharge column 88 can be located between one of the plurality of protrusions 26 and a sidewall 24.

Figure 10:
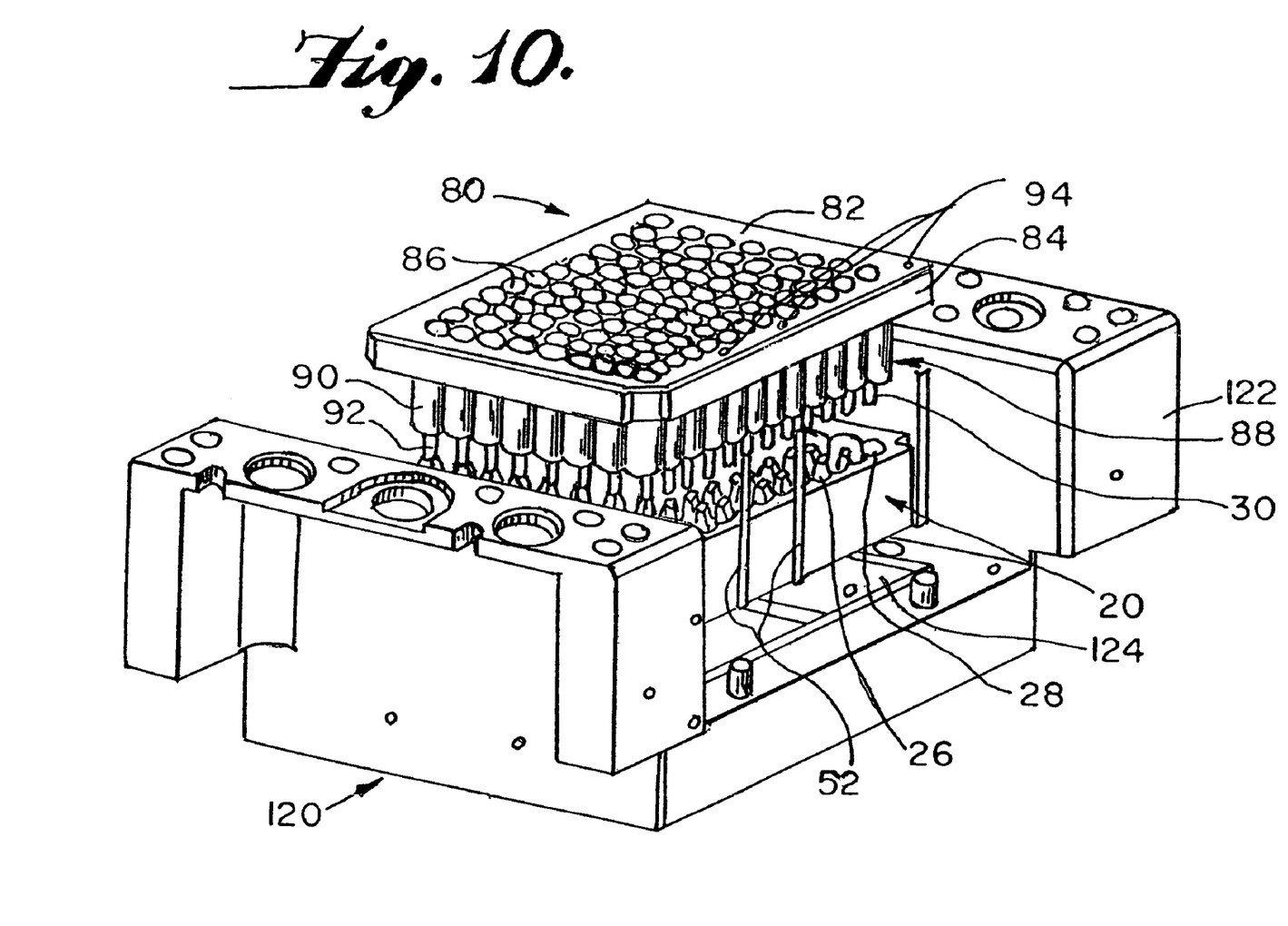
FIG. 10 is a perspective view of a purification apparatus including a sample tray, a heater module, and a carriage.

The sample purification tray and heater module can be held in housing assembly 120 by carriage frame 122 having receiving area 124, as shown in FIG. 10.

According to various embodiments, and as shown and described in U.S. patent application Ser. No. 09/552,301, filed Apr. 18, 2000, and issued as U.S. Pat. No. 6,419,827 B1, which is incorporated herein in its entirety by reference, a vent plate can be located between the heater module 10 and the receiving well array 100. The vent plate can have a plurality of though holes for nozzle tips corresponding to the though holes for nozzle tips in the heater module, and corresponding to the wells in the receiving well array, to allow fluid communication from the sample purification tray through the heater module and vent plate to the receiving well array. Apertures or vents can extend through the vent plate. At least one aperture can be located adjacent each through hole for a nozzle tip in the vent plate. The apertures permit fluid communication between the regions above and below the vent plate. By this construction, a vacuum drawn from beneath the vent plate will extend to the regions above the vent plate. The vent plate material can be the same as the material used to form the heater module.

According to various embodiments, an aerosol guard or other cross-flow restrictor, as described, for example, in U.S. patent application Ser. No. 09/182,946, filed Oct. 29, 1998, issued as U.S. Pat. No. 6,159,368, can be located between heater module 10 and vent plate 70, or between heater module 10 and sample well tray 100. The aerosol guard can prevent aerosols from each of sample wells 108 from cross-contaminating other sample wells. The aerosol guard can allow the passage of gases, but not aerosols, therethrough. The aerosol guard can be placed immediately adjacent and below heat source 40 of heater module 10 or, if tray 60 is used, immediately adjacent and below tray 60 of heater module 10. According to various embodiments, the aerosol guard can be placed immediately adjacent and below a vent plate. The aerosol guard can include a plurality of through holes for nozzle tips positioned substantially in alignment with one or more of through holes 54 for nozzle tips of heat source 40, through holes 66 for nozzle tips of tray 60, and through holes 72 for nozzle tips of heat plate 70, and also substantially in alignment with openings 106 in top plate 102 of sample well tray 100. At least the nozzle tips of discharge columns 88 can pass through the through holes for nozzle tips of the aerosol guard and can be in fluid communication with sample wells 108 through openings 106 of the sample well tray 100. The aerosol guard can be made of a flexible or non-flexible material and the material can be capable of withstanding the temperatures associated with use of heater module 10. The aerosol guard material can be substantially non-reactive with the chemicals and/or biological components of the sample. The aerosol guard can be made from foam-like material. The aerosol guard can be a porous, hydrophilic polymer material, such as, for example, ethyl vinyl acetate. Other suitable materials for the aerosol guard are apparent to those of ordinary skill in the art.

Various embodiments and details of the vent plate and aerosol guard can be found in related co-pending U.S. patent application Ser. No. 10/104,335, U.S. Pat. No. 6,419,827 B1, and U.S. Pat. No. 6,159,368, all of which are incorporated herein in their entireties by reference.

As shown, for example, in FIG. 8, when the sample purification tray 80 is fitted with heater module 10, at least the nozzle tips of the discharge columns 88 can protrude through discharge column receptacles 28 and through holes 30 for nozzle tips in heat distribution plate 20, through through holes 54 for nozzle tips in heat source 40, and, optionally, if tray 60 is used, through through holes 66 for nozzle tips in tray 60, to extend below tray 60 or heat source 40 and be in fluid communication with sample well tray 100.

According to various embodiments, any sample placed in sample purification tray 80 through an opening 86 into a discharge column 88 can flow through the discharge column 88 and can emerge from respective discharge opening 96 into respective opening 106 of the top plate 102 of the sample well tray 100, and can proceed through opening 106 into respective sample well 108. According to various embodiments, the number of discharge columns 88, discharge openings 96, through holes 30, 54 and 66 for nozzle tips, and openings 106 in sample well tray 100 are equivalent. According to various embodiments, the number of openings 106 in sample well tray 100 can be less than the number of discharge columns 88, discharge openings 96, and through holes 30, 54, and 66 for nozzle tips, such that multiple adjacent discharge columns 88 and corresponding discharge openings 96 are in fluid communication with a single opening 106 of sample well tray 100.

Heater module 10 is capable of providing heat to sample purification tray 80 such that samples can be heated before and/or during passage through discharge columns 88 of sample purification tray 80. Heater module 10 can be, for example, capable of maintaining a temperature or raising a temperature of samples in the respective plurality of discharge columns 88 of sample purification tray 80 during the period of time it takes for the samples to pass through the discharge columns 88.

Figure 11:
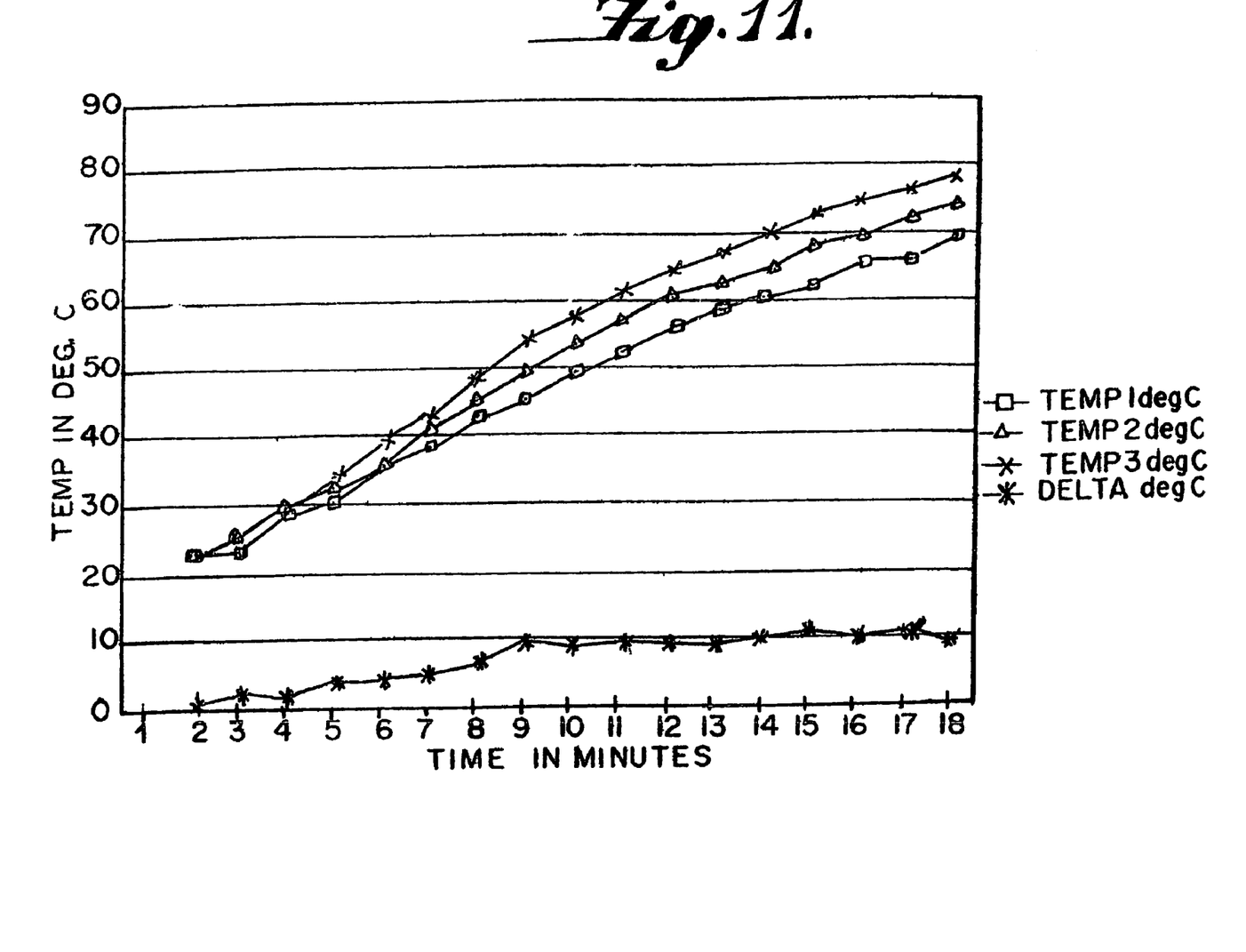
FIG. 11 is a graph illustrating the temperature rate increase of water using a heater module according to various embodiments.

According to various embodiments, heater module 10 is capable of heating at a rate sufficient to heat 1 ml of water at 1° C. per minute or greater, when the water disposed in a thermally conductive polymeric receptacle having an area of about three cm$^2$ in thermal contact with the heater module. For example, as shown in FIG. 11, the heater module 10 can raise the temperature of 1 ml of water in a 0.25 inch diameter column of a sample purification tray 80 fitted into the heater module 10, from about 23° C. to about 65° C. in 20 minutes or less. The heater module 10 can be capable of providing heat sufficient to heat samples to a temperature in a range of from about 5° C. to about 100° C. The heater module 10 can be capable of providing heat sufficient to heat samples to a temperature in a range of from about 20° C. to about 70° C.

One or more of the heat distribution plate 20, heat source 40, and tray 60 of the heater module 10 can be constructed from a thermoconductive material. According to various embodiments, each of the heat distribution plate 20, heat source 40, and tray 60 are made from a thermoconductive material. The thermoconductive material can be a metallic thermoconductive material, such as aluminum, iron, tantalum, titanium, copper, or alloys thereof. The thermoconductive material can be a thermoconductive polymeric material capable of withstanding temperatures in the range or from about 5° C. to about 100° C. without deforming, cracking or melting. The polymeric material can include a thermoconductive filler material. The filler material can be one or more different fillers selected from a carbon material, boron nitride, and metallic materials, for example, aluminum, alumina, copper, magnesium, and brass, or a combination thereof.

According to various embodiments, heat distribution plate 20 can be constructed of a substantially rigid, thermoconductive material. According to various embodiments, the plurality of protrusions 26 can be made of the same material as sidewalls 24. The heat distribution plate 20, including bottom portion 22, sidewalls 24, and the plurality of protrusions 26, can be made of a substantially unitary construction. For example, the heat distribution plate 20 can be molded or machined to include the plurality of protrusions 26 and the sidewalls 24. According to various embodiments, the plurality of protrusions 26 can be formed separately from bottom portion 22 and bonded thereto or otherwise attached. The sidewalls 24 can be formed separately from bottom portion 22 and bonded or otherwise attached thereto. Bonding of the plurality of protrusions 26 or sidewalls 24 to bottom portion 22 can be done by any known process, for example, bonding by epoxy or by a welding process such as heat welding or ultrasonic bonding or welding.

According to various embodiments, wherein the thermoconductive material of the heat distribution plate 20 is a polymer, the material can be a mixture of one or more polymers, one or more monomers, or of one or more polymers with at least one thermoconductive filler material. According to various embodiments, the polymer can be a liquid crystal polymer. According to various embodiments wherein a thermally conductive filler material is used, the filler material can be one or more different fillers selected from a carbon material, boron nitride, and metallic materials, for example, aluminum, alumina, copper, magnesium, and brass, or a combination thereof. Various examples of thermally conductive composite materials are described, for example, in U.S. Pat. No. 6,048,919. Exemplary thermally conductive liquid crystalline polymers (LCP) can be obtained from Cool-Polymers, Inc. under the trademarks Cool-Poly® E200, Cool-Poly® RB018, Cool-Poly® RB019, Cool-Poly® RB020, Cool-Poly® RS008, Cool-Poly® D2, Cool-Poly® RS007, and Cool-Poly® RS012.

According to various embodiments wherein a tray 60 is part of the heater module 10, the tray 60 can be made of or include any thermoconductive material as described herein. According to various embodiments, the tray 60 can be made from the same material as the heat distribution plate 20, for example, the same thermoconductive material. According to various embodiments, the heating tray can be a non-conductive material. The heating tray can be made of glass, ceramic, a polymeric material, a metal, an alloy, or a combination thereof. According to various embodiments wherein a tray 60 is included, the heat 40 source can be located against bottom portion 62 of tray 60 in a space defined by bottom portion 62 and sidewall 64. The heat source 40 can be bonded to or placed against bottom portion 62 of tray 60. The heat source 40 can be bonded or otherwise attached to a side of the bottom portion 22 of heat distribution plate 20, which can be set into tray 60 in a space defined by bottom portion 62 and sidewall 64. According to various embodiments, both a heat distribution plate 20 and a tray 60 can be used in a heater module 10 wherein both the heat distribution plate 20 and tray 60 can be made of or include aluminum. The heater module 10 can contain both a heat distribution plate 20 and a tray 60, wherein the heat distribution plate 20 and tray 60 can both be made of or include a thermoplastic material. According to various embodiments wherein the heat distribution plate 20 and tray 60 are both made from or include thermoplastic material, the heat distribution plate 20 and tray 60 can be bonded together. Heat distribution plate 20 and tray 60 can be bonded together after, for example, placing a heat source 40 between the heat distribution plate 20 and tray 60. Such bonding can be achieved by any method known to those skilled in the art, such as by the use of epoxy, thermoconductive epoxy, or thermal bonding. According to various other embodiments, the heat distribution plate 20 and tray 60 can be attached mechanically such that the heater module 10 comprising the heat distribution plate 20 and tray 60 with or without a heat source 40 therebetween can be moved as a single unit.

According to various embodiments, the heat source 40 can include any heating system known to those skilled in the art to provide uniform distribution of heat. The heat source 40 can be attached to the heat distribution plate 20, attached to the tray 60, attached to both the heat distribution plate 20 and tray 60, or set between the heat distribution plate 20 and tray 60. The heat source 40 can be made from a flexible material and can comprise a film or sheet, for example, a polyimide sheet material such as KAPTON, available from DuPont High Performance Materials, Circleville, Ohio. The heat source 40 can be a printed resistor circuit on a side of bottom portion 22 of heat distribution plate 20 or can be a printed resistor circuit on the bottom portion 62 of tray 60, wherein the printed resistor circuit is capable of generating heat. According to various embodiments wherein the heat source 40 comprises a printed resistor circuit in the form of wire layout 48, the wire layout 48 can be made from any conductive material capable of producing a predetermined, minimum, and/or maximum amount of heat. For example, the wire layout can be made from various metals or metal alloys, including gold, silver, aluminum, copper, titanium, alloys thereof, and other metals and metal alloys as known to those of ordinary skill in the art. The wire layout 48 can be set forth in a bottom layer 44 capable of accepting and holding in place the wire layout. The bottom layer 44 can be made from a flexible or non-flexible material. The bottom layer 44 can be made from silicone, a polymeric material, glass, or any other material known to those of ordinary skill in the art, including composite materials. The cover layer 46 can be made of or include any material capable of encapsulating wire layout 48 and bottom layer 44, wherein the cover layer material is capable of transferring heat from the wire layout 48 to the heat distribution plate 20. According to various embodiments, the cover layer 46 can be the same material as the bottom layer 44. According to various embodiments, the cover layer 46 can be a polymeric material. Other suitable materials are apparent to those of ordinary skill in the art.

The heat source 40 comprising the bottom layer 44, wire layout 48, and cover layer 46, can be capable of generating a predetermined amount of heat dependent upon the resistance and current input of the wire layout 48. The amount of heat capable of being generated can be changed by changing the resistance of wire layout 48, or by lowering or raising the amount of current passing through wire layout 48. Electrical current is provided to wire layout 48 through wires 50, which are connected to controller 57 by connector 56. Controller 57 can control the amount of current that passes through wires 50 to wire layout 48, and therefore the amount of heat generated by wire layout 48 and heat source 40.

According to various embodiments, heat source 40 can be formed integrally with tray 60 or heat distribution plate 20. The heat source 40 can be formed integrally with tray 60 such that bottom layer 44 of heat source 40 corresponds to bottom portion 62 of tray 60. The heat source 40 can be formed integrally with heat distribution plate 20 such that cover layer 46 of heat source 40 corresponds to bottom portion 22 of heat distribution plate 20.

According to various embodiments, a heat source can be incorporated into heat distribution plate 20. In such embodiments, heat distribution plate 20 with the incorporated heat source can be used as an alternative to or in addition to heat source 40. Wires, a wire layout, and/or a printed resistor circuit can be molded or otherwise formed within the heat distribution plate 20 having an incorporated heat source. The wires, wire layout, and/or printed resistor circuit can be molded or otherwise formed within at least one of the bottom portion 22, the sidewalls 24, and the plurality of protrusions 26. The heat distribution plate 20 with the incorporated heat source can be formed similar to the way that a steel-reinforced concrete slab is formed by pouring concrete into a mold containing a network or a grid pattern of steel rebar. For example, at least part of a network of resistors, wires, a wire layout, resistive heat elements, and/or a printed resistor circuit can be placed into a mold and a thermoconductive material that is in a molten state can be poured into the mold. When the thermoconductive material hardens, the hardened object forms the heat distribution plate 20 with the incorporated heat source. The resistors, wires, wire layout, resistive heat elements, and/or printed resistor circuit can be affixed to, inserted in, and/or embedded into the at least one of the bottom portion 22, the sidewalls 24, and the plurality of protrusions 26. The resistors, wires, wire layout, resistive heat elements, and/or printed resistor circuit can be made of various metals or metal alloys, including gold, silver, aluminum, copper, titanium, alloys thereof, and other metals and metal alloys as known to those of ordinary skill in the art. The heat distribution plate 20 with the incorporated heat source can be capable of generating a predetermined amount of heat dependent upon the resistance and current input of the wires and/or wire layout. A controller can provide current to the wires and/or wire layout via a connector. The heat distribution plate 20 with the incorporated heat source can perform in the same manner as the heat source 20 without the incorporated heat source and heat source 40.

According to various embodiments, the temperature of the sample tray heater module 10 can be monitored. The heat source 40 can include one or more heat sensor or temperature probe 52 such as a thermistor, a thermostat, a thermal protection tube, or a non-contact sensor such as an infrared sensor. The heat sensor or temperature probe 52 can be positioned such that it contacts the bottom portion 22 of heat distribution plate 20. The heat generated by heat source 40 can be controlled based upon the temperature detected or temperature readings obtained from the heat sensor or temperature probe 52. Other suitable heat sensors or temperature probe designs as known to those of ordinary skill in the art can be used with heat source 40. For example, the heat sensor or temperature probe can be located above sample purification tray 80 in order to determine the temperature of the samples inside discharge columns 88. According to various embodiments, a heat sensor or temperature probe can be located inside one or more of the discharge columns 88.

According to various embodiments, and as shown in FIG. 1, heater module 10 is designed to interact with and complement sample purification tray 80. The sidewalls 24 of heat distribution plate 20 of heater module 10 extend substantially perpendicularly or perpendicularly from a side of bottom portion 22 such that when mated with a sample purification tray 80, the sidewalls 24 of heat distribution plate 20 substantially cover discharge columns 88 of sample purification tray 80 from view. According to various embodiments, the sidewalls 24 of heat distribution plate 20 can touch a side of top plate 82 of the sample purification tray 80. According to various other embodiments, the sidewalls 24 of heat distribution plate 20 can be in contact with one or more discharge columns 88 of sample purification tray 80. The sidewalls 24 can be in contact with one or more portion of discharge column 88, for example, the second portion 92 or the first portion 90 of discharge column 88. According to various other embodiments, the sidewalls 24 of heat distribution plate 20 can be in contact with the sidewalls 84 of the sample purification tray 80. The plurality of protrusions 26 of heat distribution plate 20 can be in contact with a side of top plate 82 of the sample purification tray 80. According to various embodiments, the plurality of protrusions 26 of heat distribution plate 20 extend from heat distribution plate 20 and are located between discharge columns 88 of the sample purification tray 80. According to various embodiments, each of the plurality of protrusions 26 is in contact with one or more of the discharge columns 88. For example, one or more of the plurality of protrusions 26 can be in contact with a second portion 92, a first portion 90, or both a second portion 92 and a first portion 90, of a discharge column 88 of sample purification tray 80. At least a portion of one or more of the discharge columns 88 can substantially fit between two or more of the plurality of protrusions 26, or between one or more of the plurality of protrusions 26 and sidewall 24 of the heat distribution plate 20.

According to various embodiments, the plurality of protrusions 26 of the heat distribution plate 20 can function as a heat sink to dissipate heat by heating discharge columns 88 of the sample purification tray 80. A fan can be positioned to promote heat distribution between the plurality of protrusions 26 and heat absorption by the discharge columns 88.

According to various embodiments, one or more of through hole 30 for a nozzle tip of heat distribution plate 20, through hole 54 for a nozzle tip of heat source 40, and optionally through hole 66 for a nozzle tip of tray 60, can be sized so as to closely fit the profile of discharge column 88 of sample purification tray 80. One or more through hole 30, 54, or 66 for a nozzle tip can be sized to closely mate with a corresponding discharge column 88 so that bending of the discharge column 88 can be minimized. According to various embodiments, the spacing of one or more through hole 30, 54, or 66 for a nozzle tip, can assist in maintaining equal spacing between the discharge columns 88.

According to various embodiments, a purification apparatus comprising a sample purification tray 80, a heater module 10, a sample well tray 100, optionally a vent plate, and optionally an aerosol guard, can be formed using the components described herein. For purification of a sample, the purification apparatus can be placed under vacuum conditions to create a pressure differential. According to various embodiments wherein a vacuum condition will be endured, openings and seams in the purification apparatus, and between the purification apparatus and a housing assembly 120, can be sealed using any sealant capable of maintaining vacuum conditions as known to those of ordinary skill in the art. An exemplary sealant can be made from organopolysiloxane materials. Other suitable sealants as known to those of ordinary skill in the art can be used such as those described, for example, in U.S. Pat. Nos. 5,929,138; 5,079,300; 5,037,667; 4,950,546; 4,777,063; 4,680,233; and 4,595,635.

A purification apparatus as described herein can be used for filtering samples, such as biological materials, and directing the filtered samples into a plurality of respective sample wells in a sample well tray or receiving well array. Any procedure known to those of ordinary skill in the art can be used to filter the samples. For example, purification of a nucleic acid such as RNA for polymerase chain reaction (PCR) analysis can be performed using the purification apparatus set forth herein. Besides RNA purification, other processes such as, but not limited to, purification of DNA, extraction and/or purification of RNA or DNA from blood, and extraction and/or purification of proteins, can be performed using the purification apparatus described herein. The purification apparatus can be used for purifying specific sequences of DNA or RNA by varying, for example, the filter element of the sample purification tray, the chemistries used to react with the sequences, and/or reagents. The purification apparatus can be used for processing biological or chemical samples, such as by filtration, separation, species immobilization, or other chemical or physical action or reaction of two or more chemical or biological substances.

Various purification, filtration, separation, immobilization, or reaction processes can be enhanced by heating during processing. The purification apparatus as described herein can be heated during processing of samples. The ability to heat a sample tray of a purification apparatus as described herein allows the apparatus to be used for a wide range of processes. Heating can increase the kinetic energy of the samples in the discharge columns of the sample purification tray, which can result in a decrease in the amount of time required for reaction, facilitate a more thorough mixing of the sample, catalyze a reaction, and/or lower viscosity to facilitate discharge of the sample through the filtering medium. Maintaining the temperature of a sample during filtering, purification, separation, immobilization, or reaction can improve or maintain viability of the sample, and/or decrease reaction times of later process steps. According to various embodiments, the use of a heater module as described herein in a purification apparatus can avoid or eliminate compatibility issues of biological samples, such as PCR material, by indirectly heating the samples of such materials and not directly heating the samples themselves. The purification apparatus described herein can be used to maintain a constant temperature, or to fluctuate the temperature of a sample during processing.

The purification apparatus as described herein can be used, for example, in manual or automated workstations for sample preparations. For example, one or more of the sample purification tray, heater module and sample well tray of various embodiments can be used in the ABI PRISM 6700 Automated Nucleic Acid Workstation or the ABI PRISM 6100 Workstation, both of which are manufactured by Applied Biosystems. One or more of the sample purification tray, heater module, and sample well tray can also be suitable for use with a wide variety of available automated or manual sample preparation workstations, which workstations are known to those of ordinary skill in the art.

According to various embodiments, the heater module described herein can be used to heat a sample purification tray while the sample purification tray is being installed in a housing assembly. Interrelation of a sample purification tray and carriage frame of a housing assembly is set forth, for example, in U.S. Pat. No. 6,419,827 B1, incorporated herein in its entirety by reference.

According to various embodiments, one or more samples can be placed in one or more of the plurality of discharge columns 88 of a sample purification tray 80 such that the samples pass through the discharge columns 88, through respective discharge openings 96, and into respective openings 106 of sample wells 108 of a sample well tray 100. The samples can be heated by heater module 10 while they are passed through discharge columns 88. The heat distribution plate 20 of heater module 10 can surround and provide constant and uniform heating to each of the plurality of the discharge columns 88 and thereby uniformly heat the sample or samples passing through the discharge columns 88. The heater module 10 can be used to preheat the sample purification tray 80, to heat the sample purification tray 80 while a sample passes therethrough, or to preheat and heat the sample purification tray 80 during use.

Various examples of the components described herein are further set forth and described, for example, in co-pending related U.S. patent application Ser. No. 10/104,335, U.S. Pat. No. 6,419,827 B1, and U.S. Pat. No. 6,159,368. All publications cited herein are incorporated by reference in their entireties.

Those skilled in the art can appreciate from the foregoing description that the broad teachings of the present invention can be implemented in a variety of forms. Therefore, while this invention has been described in connection with certain embodiments and examples thereof, the true scope of the invention should not be so limited. Various changes and modifications can be made without departing from the scope or spirit of the invention, as defined by the appended claims.

What is claimed is:

1. A heater module comprising:
   a heat distribution plate comprising a bottom portion comprising a first surface, an opposite second surface, and a plurality of through holes arranged in an array passing through the heat distribution plate from the first surface to the second surface; and
   an electrically resistive element heater in or on the heat distribution plate and adapted to heat the heat distribution plate,
   wherein the bottom portion further comprises a plurality of protrusions spaced from one another and extending away from the first surface.

2. The heater module of claim 1, wherein the electrically resistive element heater comprises a foil heater.

3. The heater module of claim 1, wherein the electrically resistive element heater is printed on the heat distribution plate.

4. The heater module of claim 1, wherein the electrically resistive element heater comprises a plurality of heaters.

5. The heater module of claim 1, wherein the heat source further comprises a temperature sensor.

6. The heater module of claim 1, wherein the heat distribution plate comprises a polymeric material.

7. The heater module of claim 1, wherein the heat distribution plate comprises a metallic material.

8. The heater module of claim 7, wherein the metallic material is selected from aluminum, copper, titanium, tantalum, iron, alloys thereof, and combinations thereof.

9. A sample purification apparatus comprising:
   a heater module, the heater module comprising a bottom portion comprising a first surface, an opposite second surface, a plurality of through holes passing through the heat distribution plate, and a heat source incorporated in the heat distribution plate and adapted to heat the heat distribution plate; and
   a sample purification tray comprising a first surface, a second surface opposing the first surface, and a plurality of purification columns extending away from the second surface, each purification column including a distal tip portion including an outlet opening through which sample liquid in the purification column can be discharged from the purification column, wherein the plurality of purification columns are spaced from one another in an array having a configuration adapted such that the outlet openings of the plurality of purification columns are capable of being aligned with the plurality of through holes through the heat distribution plate.

10. The purification apparatus of claim 9, wherein the heater module further comprises sidewalls extending away from the first surface.

11. The purification apparatus of claim 9, wherein the bottom portion further comprises a plurality of protrusions spaced from one another and extending away from the first surface.

12. A purification method comprising:
   providing the sample purification apparatus of claim 9;
   disposing a plurality of respective samples in the purification columns of the sample purification tray;
   activating the heat source of the heater module to provide heat to the heat distribution plate; and
   passing the samples through the purification columns and out the respective outlet openings while the heat distribution plate heats the samples.

13. The method of claim 12, comprising heating the respective samples to a temperature of from about 20° C. to about 70° C.

14. The method of claim 12, comprising heating the respective samples at a rate of about 1° C. per minute or greater.

15. The method of claim 12, wherein the heat source of the heater module is activated before the plurality of respective samples is disposed in the purification columns of the sample purification tray.

* * * * *